US00PP35116P2

(12) United States Plant Patent
von Tubeuf

(10) Patent No.: US PP35,116 P2
(45) Date of Patent: Apr. 18, 2023

(54) ***BIDENS* PLANT NAMED 'KLEBF21468'**

(50) Latin Name: *Bidens ferulifolia*
Varietal Denomination: KLEBF21468

(71) Applicant: KLEMM + SOHN GMBH & CO. KG, Stuttgart (DE)

(72) Inventor: Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/869,499

(22) Filed: Jul. 20, 2022

(51) Int. Cl.
*A01H 5/02* (2018.01)
*A01H 6/14* (2018.01)

(52) U.S. Cl.
USPC ..... Plt./410
CPC ..... *A01H 6/14* (2018.05)

(58) Field of Classification Search
USPC ..... Plt./410
CPC ..... A01H 6/14; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new *Bidens* plant particularly distinguished by red and yellow flowers, compact vigor, and late earliness, is disclosed.

1 Drawing Sheet

Genus and species: *Bidens ferulifolia.*
Variety denomination: 'KLEBF21468'.

BACKGROUND OF THE NEW PLANT

The present invention comprises a new and distinct variety of *Bidens*, botanically known as *Bidens ferulifolia* and hereinafter referred to by the variety name 'KLEBF21468'. 'KLEBF21468' originated from a controlled-cross between the commercial female *Bidens* variety Hawaiian Flare Compact Bicolour Star (Patent status unknown) and the proprietary male *Bidens* variety 'BF-2017-7030' (unpatented).

In August 2018, the two *Bidens* parental lines Hawaiian Flare Compact Bicolour Star and 'BF-2017-7030' were crossed in Stuttgart, Germany and seeds were obtained. The seeds were sown and plants were grown for evaluation. A plant line was selected in May 2019 and subsequently named 'KLEBF21468'. In May 2019 'KLEBF21468' was first vegetatively propagated by vegetative cuttings in Stuttgart, Germany. 'KLEBF21468' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Red and yellow flowers;
2. Compact vigor; and
3. A late earliness.

DESCRIPTION OF THE PHOTOGRAPH

This new *Bidens* plant is illustrated by the accompanying photograph which shows an overall view of the plant. The photograph is of an approximately 11-week-old plant grown in Stuttgart, Germany in February 2022. The colors shown are as true as can be reasonably obtained by conventional photographic procedures.

DESCRIPTION OF THE NEW VARIETY

The following detailed descriptions set forth the distinctive characteristics of 'KLEBF21468'. The data which define these characteristics were collected from asexual reproductions carried out in Stuttgart, Germany. Data was collected on plants grown 4-months old in Stuttgart, Germany grown in a greenhouse in April 2022. Color references are to The R.H.S. Colour Chart of The Royal Horticultural Society of London (R.H.S.), 5$^{th}$ edition (2007).

Classification:
- *Family.*—Asteraceae.
- *Botanical.*—*Bidens ferulifolia.*
- *Designation.*—'KLEBF21468'.

Parentage:
- *Female parent.*—Hawaiian Flare Compact Bicolour Star (Patent status unknown).
- *Male parent.*—BF-2017-7030 (unpatented).

Plant:
- *Habit.*—Upright to semi-trailing.
- *Height.*—8.0 cm.
- *Spread.*—16.0 cm.
- *Life cycle.*—Annual.
- *Time to produce a rooted cutting.*—3 to 4 weeks.
- *Hardiness.*—USDA zone 8-11.
- *Root description.*—Fine, white RHS NN155D.
- *Rooting habit.*—Freely branching.
- *Time to bloom from propagation.*—7 weeks from potting date.
- *Branching habit.*—Freely branching.

Lateral branches:
- *Quantity per plant.*—More than 30.
- *Strength.*—Weak to medium.
- *Shape.*—Cylindrical.
- *Texture.*—Sparsely pubescent.
- *Color.*—RHS 143C.
- *Pubescence.*—Present.
- *Diameter.*—0.15 cm.
- *Length.*—5.0 cm to 6.0 cm.
- *Internode length.*—1.5 cm to 3.0 cm.

*Anthocyanin*.—Slight anthocyanin coloration on lower parts (small spots, RHS not applicable).

Leaves:

*Arrangement*.—Opposite.
*Length*.—2.0 cm to 2.5 cm.
*Width*.—1.5 cm to 2.0 cm.
*Shape*.—Pinnate compound (3 single leaves composed to one leaf).
*Apex*.—Acute.
*Base*.—Attenuate (leaflets).
*Margin*.—Lobed to serrate (leaflets).
*Texture*.—Upper surface: Slightly haired. Lower surface: Smooth.
*Venation pattern*.—Pinnate.
*Color of developing leaves* (*immature*).—Upper surface: RHS 143A. Lower surface: RHS 139D. Venation color: Upper surface: RHS 142C. Lower surface: RHS 142C.
*Color of fully expanded leaves* (*mature*).—Upper surface: RHS N137D. Lower surface: RHS 137C. Venation color: Upper surface: RHS 142C. Lower surface: RHS 142C.
*Petiole*.—Length: 0.5 cm to 1.0 cm. Diameter: 0.1 cm. Color: RHS 143C to RHS 143D. Texture: Slightly haired.

Inflorescence:

*Appearance and type*.—Composite.
*Flowering habit*.—Continuous.
*Lastingness of inflorescence on the plant*.—7 to 10 days.
*Number of inflorescences and buds per plant*.—About 20 inflorescences open at the same time plus about 20 flower buds.
*Fragrance*.—Present, honey-like.
*Natural flowering season*.—Spring through summer and fall.
*Diameter*.—4.0 cm to 5.0 cm.
*Depth*.—0.5 cm.
*Disc diameter*.—0.9 cm to 1.1 cm.

Flower buds:

*Length*.—0.5 cm to 0.6 cm.
*Diameter*.—0.4 cm to 0.5 cm.
*Surface texture*.—Slightly pubescent.
*Shape*.—Round, flattened on top.
*Color*.—Varying between RHS 143C and RHS N144D.

Ray florets:

*Quantity per inflorescence*.—8.
*Length*.—About 2.0 cm.
*Width*.—0.8 cm to 1.0 cm.
*Shape*.—Ovate.
*Apex*.—Obtuse, but showing 1 sharp tip on top in the middle plus 2 broader tips left and right (depth less than 0.05 cm).
*Base*.—Fused bottom 0.1 cm.
*Margin*.—Entire.
*Color, when opening*.—Upper surface: Close to RHS N34A (Reddish-orange). Lower surface: RHS 34B (reddish) and RHS 9A (yellow) stripes.
*Color, when fully open*.—Upper surface: Close to RHS 33B (not well represented in RHS) with RHS 9A (yellowish) background. Lower surface: Close to RHS 34B (but very weak, overlayed by yellow RHS 9A).
*Color descriptions above refer to upper half of the ray-flowers, lower half is yellow RHS close to 9A.*
*Surface texture* (*both upper and lower surfaces*).—Smooth.

Disc florets:

*Quantity per inflorescence*.—About 50.
*Length*.—0.4 cm (when open 0.6 cm).
*Width*.—0.05 cm.
*Shape*.—Tubular.
*Apex*.—Five-pointed.
*Base*.—Fused.
*Margin*.—Entire.
*Color, when opening*.—Upper surface: Not applicable (too small to define). Lower surface: RHS 149D/transparent.
*Color, when fully open*.—Upper surface: Not applicable (too small to define). Lower surface: RHS 10B/transparent.
*Surface texture* (*both upper and lower surfaces*).—Smooth.

Phyllaries:

*Quantity per inflorescence*.—About 6.
*Length*.—0.3 cm.
*Width*.—0.1 cm at the bottom.
*Shape*.—Triangular.
*Apex*.—Acute.
*Base*.—Fused.
*Margin*.—Entire.
*Surface texture*.—Upper surface: Smooth. Lower surface: Smooth.
*Color*.—Upper surface: RHS 144D. Lower surface: RHS 1C margins, RHS 177A apex, RHS 144D bottom.

Calyx:

*Length*.—0.5 cm to 0.6 cm.
*Width*.—0.1 cm.
*Shape*.—Between spatulate and cuneate.
*Apex*.—Mucronate.
*Base*.—Fused.
*Margin*.—Entire.
*Surface texture*.—Upper surface: Smooth. Lower surface: Slightly pubescent.
*Color* (*both surfaces*).—RHS N137D.

Peduncle:

*Length*.—About 0.0 cm.
*Diameter*.—0.1 cm.
*Color*.—RHS 143B.
*Texture*.—Slightly haired.
*Strength*.—Relatively weak.

Reproductive organs:

*Androecium*.—Present on disc florets only. Quantity of stamens per floret: 5. Filament length: 0.4 cm. Filament color: RHS 200A. Anther length: Approximately 0.1 cm to 0.15 cm. Pollen amount: Abundant. Pollen color: Between RHS 17A and RHS 21A.
*Gynoecium*.—Present on ray florets only. Quantity of pistils per floret: 1. Pistil length: 0.3 cm. Style length: 0.2 cm. Style color: RHS 15A. Stigma shape: Two parted. Stigma color: RHS 15A. Ovary color: RHS 149C.

Fruit and seed set: None observed.

Disease and pest/insect resistance: None observed.

COMPARISON WITH PARENTAL LINES AND KNOWN VARIETY

'KLEBF21468' is distinguished from its parents as described in Table 1:

TABLE 1

| Comparison with Parental Lines | | | |
|---|---|---|---|
| Trait | 'KLEBF21468' | Female parent Hawaiian Flare Compact Bicolour Star | Male parent 'BF-2017-7030' |
| Vigour | Compact | Very compact | Vigorous |
| Earliness | Late | Very early | Early |

'KLEBF21468' can be compared to the commercial variety 'Bidy Boom Fireside'(not patented). Differences between the two varieties are described in Table 2:

TABLE 2

| Comparison with Similar Variety | | |
|---|---|---|
| Trait | 'KLEBF21468' | Commercial line 'Bidy Boom Fireside' |
| Vigour | Compact | Medium |
| Earliness | Early | Second early |

I claim:

1. A new and distinct cultivar of *Bidens* Plant Named 'KLEBF21468' as described and illustrated herein.

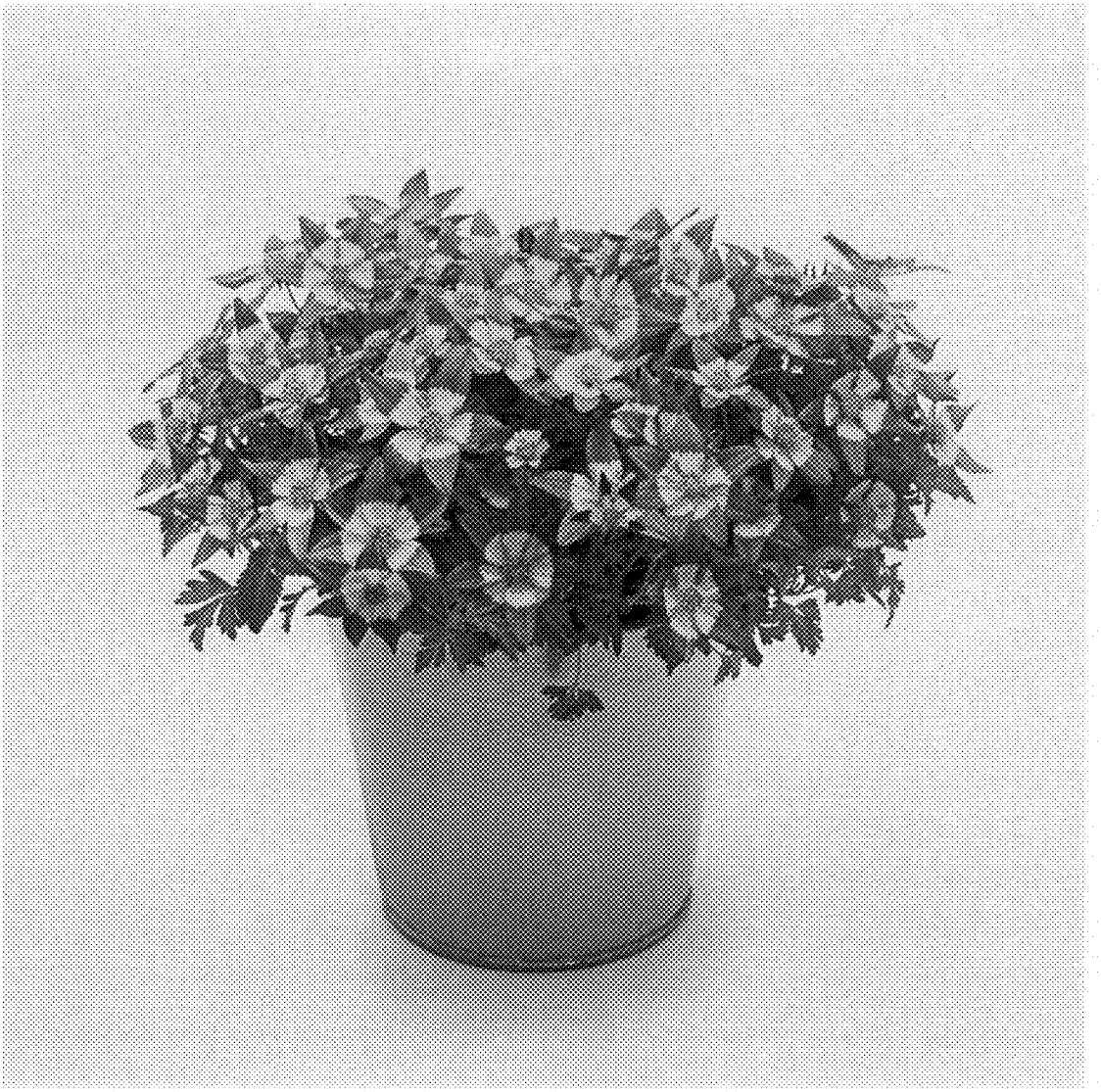

* * * * *